United States Patent [19]
Vnek et al.

[11] 3,951,937
[45] Apr. 20, 1976

[54] LARGE SCALE PURIFICATION OF HEPATITIS TYPE B ANTIGEN USING POLYETHYLENE GLYCOL

[75] Inventors: John Vnek, New York, N.Y.; Alfred M. Prince, Stanford, Conn.

[73] Assignee: The Community Blood Council of Greater New York, Inc., New York, N.Y.

[22] Filed: Dec. 20, 1973

[21] Appl. No.: 426,825

[52] U.S. Cl............. 260/112 B; 424/88; 424/89; 195/1.5
[51] Int. Cl.² .......................................... C07G 7/00
[58] Field of Search ................................ 260/112 B

[56] References Cited
UNITED STATES PATENTS

| | | | |
|---|---|---|---|
| 3,636,191 | 1/1972 | Blumberg et al. | 424/89 |
| 3,790,552 | 2/1974 | Johnson et al. | 260/112 B |
| 3,838,144 | 9/1974 | Leach | 260/112 R |

OTHER PUBLICATIONS
Laboratory Manual of Analytical Methods of Protein Chemistry, Alexander et al. 1960, pp. 70–72.

*Primary Examiner*—Howard E. Schain

[57] ABSTRACT

Highly purified type B hepatitis antigen (HB Ag) is produced from fluid blood material containing such antigen by subjecting blood material containing naturally occurring HB Ag to a double precipitation with polyethylene glycol. In each precipitation, the pH of the fluid blood material is maintained at approximately 4.4 to 4.7 and a polyethylene glycol concentration of approximately 4.0 to 4.5 weight per cent is used. Particularly good results are obtained if the temperature of the material is maintained in the range of 0° to 8°C after the polyethylene glycol has been added. The antigen thus obtained may be further purified by absorption of impurities to hydroxy apatite, followed by isopycnic banding and zonal ultracentrifugation. Hydroxy apatite column chromatography is used to separate the purified antigen into three separate populations of particles.

15 Claims, 7 Drawing Figures

100 nm

FRACTION II 100 nm

FRACTION II 100 nm

FRACTION III

LARGE SCALE PURIFICATION OF HEPATITIS TYPE B ANTIGEN USING POLYETHYLENE GLYCOL

ACKNOWLEDGEMENT OF H.E.W. SUPPORT

The invention described herein was made in the course of or under a grant from the National Institutes of Health, Department of Health, Education and Welfare.

BACKGROUND OF THE INVENTION

1. Field of the Invention

The present invention relates to the field of immunology generally, and more particularly to a large scale procedure for producing commercial quantities of highly purified type B hepatitis antigen (HB Ag) which may be used in the commercial production of a vaccine against type B hepatitis infections.

2. Description of Prior Observations and Developments

An antigen detected during the incubation period and early clinical course of post-transfusion serum hepatitis is discussed by Prince, *Proc. Nat. Acad. Sci. U.S.A.* 60:814–821 (1968). This antigen appears to be identical to the so-called Australia antigen (See Prince, *Lancet*, 2:462–463 (1968); Blumberg, Sutnick and London, *J. Am. Med. Assoc.* 207:1895–1896 (1969); and Wright, McCollum and Klatskin, *Lancet* 2:118–121 (1969), and an exchange of reference reagents has established identity between this antigen and the "hepatitis antigen" of Gocke and Kavey, *Lancet* 1:1055–1059 (1969). The antigen has been described by Prince, Hargrove, Szmuness, Cherubin, Fontana and Jeffries, *N. Engl. J. Med.* 282:287–291 (1970) as being specific for the virus of serum hepatitis, a virus which appears to be a major cause of sporadic hepatitis in urban adults, regardless of the presence or absence of parenteral exposure to blood or blood products.

The antigen associated with such serum hepatitis infections has previously been called by a variety of names such as Australia antigen, SH antigen, Au/Sh antigen, HAA, etc., and each of these names has had its supporters. However, each also has inherent defects. Geographic names make life difficult for students and physicians and HAA ignores the evident specificity of this antigen for infections with type B hepatitis virus. The term SH, has the unfortunate connotation that this antigen is associated with a virus transmissible only by "serum" or blood products; however, many lines of evidence now indicate clearly that hepatitis B virus (serum hepatitis virus) is also "infectious". Thus, the continued use of the term "serum hepatitis" is likely to result in more confusion than clarification. For this reason a special subcommittee was appointed by the National Research Council of the U.S. National Academy of Sciences to attempt, among other things, to suggest a better terminology. The terminology chosen returns to the classical terms hepatitis type A virus and hepatitis type B virus, which were employed in the 1940's and 50's. The antigen therefore logically becomes hepatitis B antigen (HB Ag) and the antibody directed towards this antigen becomes hepatitis B antibody (HB Ab). Such terminology will be used herein.

In 1964 Blumberg, Bull, *N.Y. Acad. Med.* 40:377–386 (1964) described the discovery of what then appeared to be another human serum protein polymorphism. An antibody was detected in the serum of a multiply transfused hemophiliac which reacted in the Ouchterlony technique with an antigen which was not β-lipoprotein and which was found to be present in the sera of a proportion of certain foreign populations and in the sera of some patients with leukemia. The antigen was called the Australia antigen since it was initially detected in the serum of an Australian aborigine. Family studies appeared to support the hypothesis that this antigen was a genetically determined isoantigen. The Australia antigen was subsequently shown to be present in about 25% of institutionalized patients with Down's syndrome.

A chance observation by Blumberg provided grounds for a new interpretation of the prior findings discussed above. Serial blood samples were obtained from a child with Down's syndrome. Although the child did not initially have detectable antigen, a subsequent sample gave positive results. Clinical data revealed that at almost the same time the child developed hepatitis. It was then found that the antigen was present in 5 out of 48 sera from patients with viral hepatitis.

These date were compatible with at least three hypotheses: (1) that the antigen was a genetically determined serum isoantigen whose presence correlated with susceptibility to a variety of diseases or disease agents, e.g., leukemia, mongolism, hepatitis (2) that the antigen was a genetically determined isoantigen whose expression depended on the presence of a "derepressing" virus; and (3) that the antigen was specifically associated with a virus causing one or more of these conditions.

At first, the latter hypothesis was considered to be the least likely, since it was not anticipated that a viral antigen would circulate in healthy carriers in quantities sufficient for detection by an insensitive immunodiffusion assay. However, the results of a collaborative study by Prince and Blumberg of the physical characteristics of the antigen supported the third hypothesis since the antigen was found to be associated with a particle that sedimented at the rate of a small virus-like particle.

A specific association between Australia antigen and hepatitis was, however, not made until the composition of the agar employed for the immunodiffusion test had been changed. The precipitation lines were only then sufficiently clear to permit identity testing. The results obtained with the recently developed immunodiffusion system are described by Prince, *Proc. Nat. Acad. Sci.* 60:814–821 (1968).

Jokelainen, Krohn, Prince, and Finlayson, *J. Virol* 6:685–689 (1970) investigated the structural aspects of hepatitis B antigen-containing particles with an electron microscope and confirmed the existence of large spherical particles (ca. 43 nm) and smaller (ca. 20 nm) rod- and sphere-shaped particles. The larger particles seem to include outer and inner membranes and a core as seen by positive staining techniques. The outer membranes of the large particles appear to be similar to the 20-nm diameter spheres and rods known to possess the hepatitis B antigen. Each of the three kinds of particles appears to contain the hepatitis B antigen, because they are all clumped by hepatitis B antiserum.

Occasional large particles have projections with a structure identical to that of the rod forms, and constrictions along these in some instances give rise to an appearance suggesting a series of small spherical particles. These findings appear to agree with the findings of Dane, Cameron and Briggs, *Lancet* 1:695–698 (1970) that all of these forms are produced de novo and that the small spheres and rods may represent an excessive production of membrane material.

Studies with negative staining have confirmed the virus-like appearance of the large spherical particles. Positive-staining studies have indicated three further points: (i) the larger particles have a double membrane structure; (ii) the central core of the nucleoid-like component contains material which stains with uranyl acetate; and (iii) the small spheres and rods do not contain any core material. Although uranyl acetate cannot be considered a specific stain for nucleoprotein, it is recognized as being taken up preferentially by that material and this would be expected to occur within the core of a virus. Therefore, these findings support the hypothesis that, of the three hepatitis B antigen-containing particles described, the larger 40 to 45 nm particles are most probably the actual hepatitis B virus.

Krugman et al., *J. Am. Med. Assoc.* 217:41 (1971), have provided preliminary data suggesting that serum containing HB Ag which has been inactivated by boiling for 1 minute is noninfectious, immunogenic and protective when administered to a small group of volunteer children.

Prince, Szmuness, Hargrove, Jeffries, Cherubin and Kellner have presented a comprehensive report on the status of research activities directed to investigating the hepatitis B virus specific antigen in *Perspectives in Virology*, Vol. 7, Chap. 14, pp. 241–296 (Academic Press, Inc., 1971).

It has thus been shown that HB Ag is present in serum during the incubation period of classical post-transfusion serum hepatitis. Antibody to this antigen has been found in patients who have been multiply transfused, such as patients with hemophilia and Cooley's anemia. The antibody is usually not detected in sera from convalescent patients with typical cases of viral hepatitis. The hepatitis B antigen has been found to be identical with the previously described Australia antigen, and with the "hepatitis antigen" of Gocke. The antigen has been shown to be associated with virus-like particles 20 to 25 nanometers in diameter and has an aqueous density of 1.17 in sucrose. Sera from patients with acute viral hepatitis have been tested for the presence of HB Ag to determine whether this would permit distinction between the two major types of viral hepatitis. None of 4 cases of short incubation MS-1 infection tested had detectable antigen; whereas the antigen was identified in all 8 cases of long incubation MS-2 infection tested. Correspondingly, only one out of 74 cases associated with four epidemics of infectious hepatitis, and none of 19 sporadic cases occurring in children under the age of 14 showed presence of detectable antigen; while 76 of 116 cases (66%) which occurred following exposure to contaminated needles and 25 of 43 post-transfusion cases (58%) were positive.

HB Ag has also been detected in 71 of 129 patients (55%) with viral hepatitis who gave no history of parenteral exposure.

These findings suggest that hepatitis B virus is the major cause of sporadic hepatitis in urban adults regardless of the presence or absence of parenteral exposure to blood or blood products.

HB Ag has been found to be 10 to 100 times more prevalent in tropical populations than in volunteer blood donors in New York City. These findings confirm previous results obtained by testing for the Australia antigen.

Although about 90 to 95% of patients with acute serum hepatitis in whom antigen is detected have detectable HB Ag in the blood only for short periods, some persons develop long lasting hepatitis B antigenemia. Long term persistence of antigen is also seen in clinically well individuals in all populations which have been examined.

Two to 3 percent of drug users without evidence of acute hepatitis have detectable quantities of HB Ag. By comparison, the antigen can be detected in only 0.1 percent of the volunteer blood donors in New York City. Paid blood donors, who have been reported to be at least 10 times as likely as volunteer donors to transmit hepatitis, have also been found to be 12.5 times as likely as the volunteer donors to show the presence of HB Ag in their blood.

Moreover, the hepatitis B related antigen has been found in the serum of eight of 138 chimpanzees tested. The antigen has persisted for at least 5 years in three of these animals. This antigen has not been found in the serum of 99 baboons and 11 gibbons. Antigenemic chimpanzees were found to have histologic evidence of chronic persisting hepatitis. HB Ab was found in six of 138 chimpanzees and was transient in three of these animals. The chimpanzee antigen carrier provides a useful animal model for study of the hepatitis B virus carrier state and approaches to its therapy.

It appears likely that chronic HB Ag carriers are also hepatitis B virus carriers since blood containing the antigen has given rise to hepatitis in at least five out of eight recipients in one study and nine out of 12 in a second.

The presence of HB Ag and HB Ab may be quantitatively detected by agar gel diffusion using the methodology described by Prince, *Proc. Nat'l. Acad. Sci. U.S.A.* 60:814–821 (1968), by IEOP as described by Prince and Burke, *Science* 169:593–595 (1970), by passive hemagglutination (HA) and hemagglutination inhibition (HAI) as described by Vyas and Shulman, *Science* 170:332–333 (1970) and more recently by the direct radio-immuno assay (RIA) of Ling and Overby utilizing Ausria kits supplied by Abbott Laboratories.

It has been estimated that the plasma of hepatitis B virus carriers contains about 0.1 to 1.0 mg of antigen associated protein per ml of plasma. Carrier plasma may therefore serve as a useful source of antigen for production of vaccines.

Prince, in his U.S. patent application Ser. No. 301,347, filed Oct. 27, 1972, the entirety of which is hereby specifically incorporated by reference, discloses a vaccine against type B hepatitis infections, a method for production of such a vaccine and a vaccination process which makes use of the vaccine. Specifically, Prince's vaccine includes HB Ag particles having a diameter of from about 16 to about 30 nanometers in a physiologically acceptable carrier. The vaccine is substantially free of the probably infectious HB Ag particles having a diameter of about 40 to 45 nm.

Prince, in his above identified application, makes use of a purification process involving Freon extraction and methanol precipitation followed by zonal ultracentrifugation. The zonal ultracentrifugation procedures disclosed by Bond and Hall, *J. Infect. Dis.* 125:263–268 (1972) are disclosed by Prince as being appropriate for separation and purification of HB Ag into its morphologic forms; however, the procedures disclosed are hazardous and therefore special safety facilities are required. Moreover, these zonal ultracentrifugation procedures are extremely costly and the large total quantity of material which is fed to the ultracentrifuge in the method of application Ser. No. 301,347 per unit of product results in an extremely high cost of production for the purified antigen. Accordingly, less expensive methods for production of HB Ag are desirable so that the vaccines produced therefrom will be generally available to the public at a price which can be borne without substantial hardship on the part of either the individual or the government.

Polson, in U.S. Pat. No. 3,415,804, discloses methods for fractionating mixtures of proteinacious substances using polyethylene glycol (PEG) as a dispersibility depressant to produce a liquid phase containing one fraction in dispersion and a solid phase containing a second fraction. Utilizing the Polson method, which involves the use of a pH of 7.0, a temperature of 21°C and protein concentrations less than 0.4 grams per 100 ml, a polyethylene glycol concentration greater than 12% is required to precipitate $\alpha$-globulins and albumin. Polson suggests that the higher the protein concentration, the greater the overlap between fractions. Moreover, although HB Ag is normally considered to be associated with the $\alpha$-globulin fractions, Polson does not disclose any method suitable for separating HB Ag from any of the fractions obtained from plasma. Further, very large concentrations of PEG are required by Polson to effect his desired fractionations.

De Rizzo, Pandey, Wallis and Melnik, *Inf. and Imm.* 6:335–338 (1972) have disclosed a two step method for concentrating and purifying HB Ag utilizing PEG and polyelectrolyte 60 (a cross-linked copolymer of isobutylene maleic anhydride). In the first step, plasma having a protein concentration of 79.9 mg/ml is subjected to PEG precipitation at a pH of 4.6 and a temperature of 25°C, utilizing a PEG concentration of 8%. It is indicated that the precipitate contains 100% of the original HB Ag and only 12.5% of the original proteins. The proteins in the precipitate comprise 2 mg of albumin per ml, 3 mg of $\alpha_2$-globulin per ml and 5 mg of gamma-globulin per ml. It was reported tht all of the $\alpha_1$, $\beta$, and $\beta_2$ globulins remained in the liquid phase. The precipitate thus obtained, by precipitation with PEG, was then subjected to concentration and purification of the HB Ag therein utilizing polyelectrolyte 60. Eightfold purification of the HB Ag in the PEG precipitation step was reported by De Rizzo et al.; however, attempts to utilize the De Rizzo et al. method by the present applicants have indicated that the procedure provides only a two-fold purification. Furthermore, it has been found that the De Rizzo et al. method is not reproducible as described.

Blumberg and Millman, in U.S. Pat. No. 3,636,191, have disclosed methods for producing a vaccine against viral hepatitis wherein plasma containing the antigen is subjected to ultracentrifugation, enzyme digestion, column gel filtration, differential density centrifugation in a solution of sucrose, dialysis, differential density centrifugation in a solution of cesium chloride and dialysis. The disclosed method is very expensive and is not suitable for the large scale purification of HB Ag. Further, it has been found that the antigen may be altered by proteolytic digestion. Moreover, the procedure disclosed does not appear to separate the larger HB Ag associated particles which occur in donor carrier plasma.

SUMMARY OF THE INVENTION

The shortcomings of the prior art as described above are substantially, if not completely eliminated by the provision of a completely reproducible and highly efficient method for the large scale purification of HB Ag for use in the commercial production of a vaccine against type B hepatitis infections. The method of the invention utilizes, as an initial feed, fluid blood material which contains HB Ag. In accordance with the invention, the pH of the fluid blood material is maintained at approximately 4.4 to 4.7 while approximately 4.0 to 4.5 weight percent PEG, based on the total weight of the resultant admixture, is admixed therewith to produce a precipitate which contains the antigen. The precipitate is separately recovered and sufficient water is added thereto to present an intermediate fluid material having an antigen concentration substantially the same as the original blood material. The pH of the intermediate fluid material is caused to be within the range of approximately 4.9 to 5.1 to thereby produce a precipitate containing proteinaceous material and polyethylene glycol and a fluid phase which contains the antigen. The fluid phase is separately recovered and the pH thereof is adjusted to within the range of 4.4 to 4.7. The fluid phase, while its pH is maintained within the foregoing range, is admixed with approximately 4.0 to 4.5 weight percent PEG based on the total weight of the admixture to produce a precipitate containing purified HB Ag which precipitate is separately recovered.

More specifically, it has been found that precipitation procedures utilizing PEG at a pH of 4.4 to 4.7 to produce a precipitate containing purified HB Ag may be carried out much more efficiently at a temperature in the range of approximately 0° to 8°C.

The precipitate containing the purified HB Ag may be further subjected to purification by adsorption of protein contaminants to hydroxy apatite followed by isopycnic banding and then zonal ultracentrifugation for separating the morphological forms of the antigen. While the latter procedures are quite expensive, as outlined above, the double polyethylene glycol precipitation procedure summarized above provides a highly purified material whereby the total volume fed to the ultracentrifuge per unit of recovered relatively noninfectious 20 nanometer spherical particles is substantially less than in the method described in the Prince application. Ser. No. 301,347, and as a result, the cost of production is substantially reduced.

As a further aspect of the present invention, it has been found that purified HB Ag can be separated into three different populations, each rich in a different one of the three morphological forms of HB Ag particles by a process which comprises applying a quantity of an aqueous fluid containing a substantial concentration of purified HB Ag to a hydroxy apatite chromatography column, thereafter eluting the column with a three step graduated eluant and then separately collecting at least three distinct portions of the eluate from the column. Thus, the necessity for extensive zonal ultracentrifugation is substantially reduced and possibly might be eliminated entirely.

DESCRIPTION OF THE PREFERRED EMBODIMENTS

Figure 1:
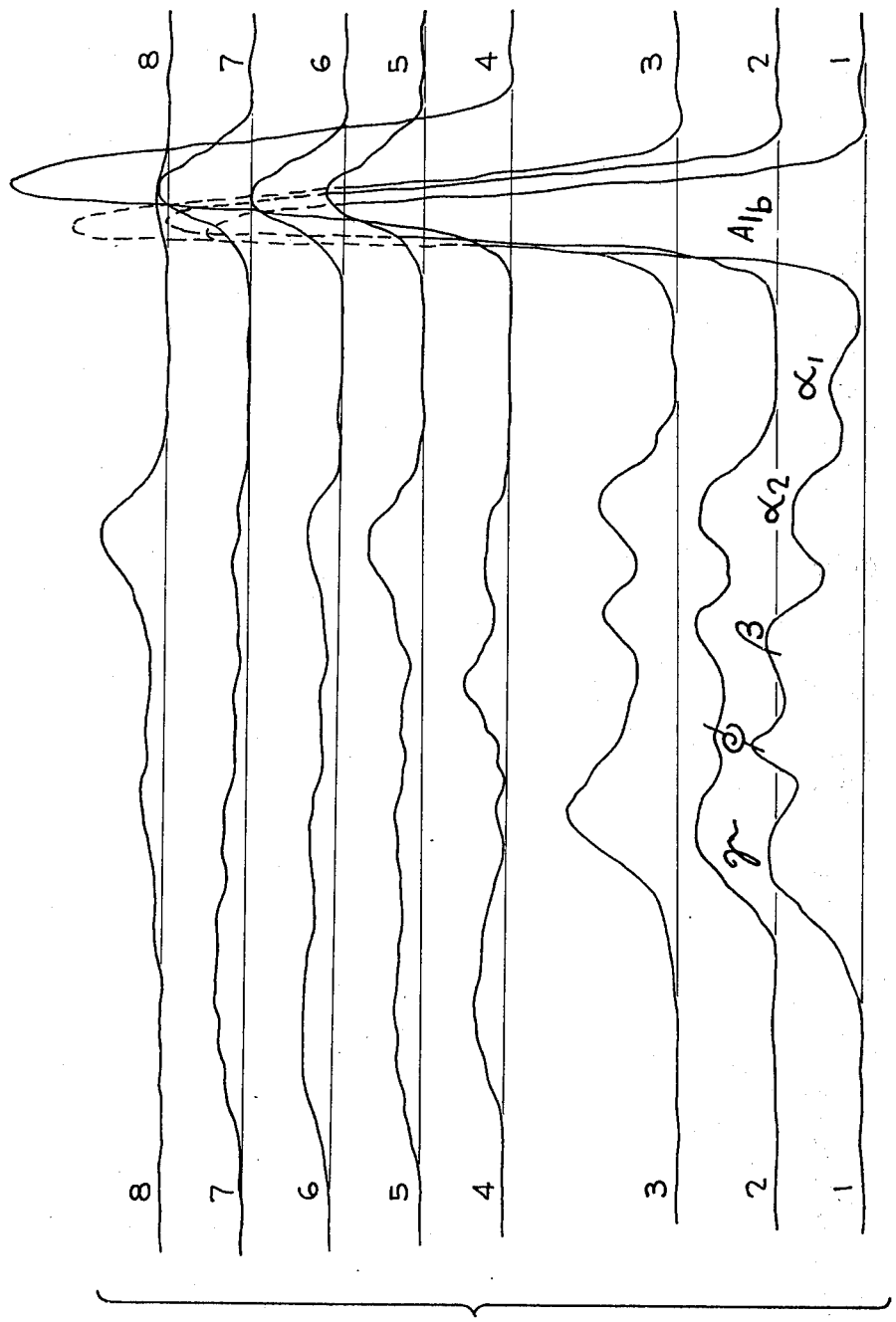
FIG. 1 is a graphical illustration of the results of cellulose acetate electrophoresis determinations of the protein contents of the materials at various stages of the polyethylene glycol precipitation procedure of the present invention.

In accordance with the present invention, purified Hb Ag is recovered quantitatively from fluid blood materials, such as blood plasma or serum which contain the antigen, by a two step precipitation procedure utilizing polyethylene glycol (PEG). PEG having a molecular weight in the range of 300 to 100,000 has been found to be suitable. A pronounced improvement is obtainable if the PEG has a molecular weight of at least 600 with an upper limit of 20,000. The best results are obtained with PEG having a molecular weight in the range of 1,500 to 20,000, say 6,000. As a rule, it is preferred to carry out the process with PEG having a limited molecular weight range, more particularly composed of molecules, the molecular weights of which are essentially within a narrow range by comparison with the total range as specified further above. However, it is sometimes possible to operate with mixtures of quite different molecular weights.

Further purification is achieved by adsorption of protein contaminants to hydroxy apatite either in a batch operation or using column chromatography procedures. In a column chromatography procedure, three distinct populations of HB Ag particles are separated. Using PEG precipitation followed by hydroxy apatite adsorption, a reduction of 1 to 1,000 sample volume can be achieved. Eventually the residual protein contaminants can be removed using the conventional techniques of isopycnic banding, zonal ultracentrifugation and exclusion chromatography on Sepharose 4B.

PEG precipitation of HB Ag removes 96% of plasma protein contaminants. Further adsorption of protein impurities to hydroxy apatite (batchwise) removes an additional 90% of protein contaminants leaving more than 50% of the original HB Ag in the supernate. After isopycnic banding and rate zonal centrifugation, the product is void of any plasma protein contaminants.

HB Ag from 8 liters of chimp plasma and from two and five liter batches of human plasma have been purified by the foregoing methods and the applicability of these methods have been proven. Using column chromatography on hydroxy apatite it has been found that HB Ag can be separated into three different populations of particles; (1) a fraction containing mostly 27–30 nm particles; (2) a fraction composed of a mixture of 27–30 nm particles; filaments and 40 nm particles and (3) a fraction containing mostly 20 nm particles.

PURIFICATION OF HEPATITIS B ANTIGEN BY POLYETHYLENE GLYCOL PRECIPITATION, BATCH TYPE HYDROXY APATITE ADSORPTION, ISOPYCNIC BANDING, AND RATE ZONAL CENTRIFUGATION

A. Polyethylene Glycol Precipitation Of Hepatitis B Antigen

De Rizzo et al., *Inf. and Imm.* 6:335–338 (1972) describe the purification of HB Ag using polyethylene glycol. Several attempts to apply the De Rizzo et al. procedure have provided only a two fold purification of HB Ag. In the following improved procedure, 96% of plasma proteins are removed with practically quantitative recoveries of HB Ag:

1. For purification, a whole unit (240 ml) of plasma containing HB Ag is used.

2. The pH of the plasma is adjusted to within the range of approximately 4.4 to 4.7 (optimum 4.6) at room temperature by adding 1.0 N HCl thereto and the precipitate formed is removed by centrifugation.

3. To the supernate from step 2, a 30% solution of PEG 6000 in distilled water is added dropwise until a 2% concentration is obtained, and the resulting admixture is left overnight in the refrigerator at a temperature of approximately 0° to 8°C to precipitate protein contaminates including fibrinogen. The supernate is clarified by centrifugation. In connection with this step it should be recognized that the addition of any substantial quantity of PEG will cause a certain quantity of proteins including fibrinogen to precipitate. Accordingly, there is really no lower limit to the quantity of PEG to be added. On the other hand, since the object of the invention is to remove impurities from HB Ag, the presence of the antigen in the precipitate from this step is to be avoided and accordingly, the upper limit for the PEG concentration is just below the level where substantial amounts of antigen will be precipitated with the fibrinogen fraction. In practice it has been found that at a concentration of 3.0 weight percent PEG will cause substantial quantities of the antigen to precipitate with the undesired fibrinogen fraction, that a concentration of 2.5 weight percent PEG is about the maximum which can be tolerated, and that a concentration of about 2.0 weight percent polyethylene glycol provides optimum results.

4. After centrifugation, the precipitate from step 3 is discarded and the PEG concentration of the supernate is adjusted to within the range of approximately 4.0 to 4.5% by weight. Thereafter, the supernate is again stored overnight in the refrigerator at a temperature of approximately 0° to 8°C. Actually, in practice it might be possible to use a PEG concentration as high as 8.0 percent by weight in this step; however, an increased PEG concentration also increases the risk of precipitating β and α globulins and albumins along with the antigen. In this connection, it should be apppreciated that while higher concentrations of polyethylene glycol might be preferable, or even requisite, at room temperature, 4.0 to 4.5 weight percent polyethylene glycol is appropriate at temperatures of 0° to 8°C.

5. The precipitate from step 4 is consolidated by centrifugation and the pellet is resuspended in approximately 200 ml of distilled water to obtain an admixture having approximately the same volume as the original plasma.

6. The bulk of the PEG and a small amount of proteins are removed from the suspension of step 5 by centrifugation after adjusting the pH of the suspension to within the range of approximately 4.9 to 5.1 (optimum 5.0) by drop-wise addition of 1.0 N NaOH. Generally a white cloud will appear during this adjustment.

7. The pH of the clear supernate from step 6 is readjusted to approximately 4.4 to 4.7 (optimum 4.6) by drop-wise addition of 1.0 N HCl and PEG is added until a final concentration of approximately 4.0 to 4.5% by weight is reached. The materials are again stored overnight in the refrigerator at approximately 0° to 8°C and are thereafter centrifuged. It is to be noted that the same considerations discussed in connection with step 4 apply here also.

8. The precipitate from step 7 which contains the antigen, is resuspended in approximately 100 ml of distilled water to obtain an admixture having approximately one-half of the volume of the original plasma.

The foregoing purification can be followed in FIG. 1, which illustrates the results of protein distribution by cellulose acetate electrophoresis after each individual step of the purification.

In FIG. 1, line 1 represents and illustrates the protein fractions present in the original HB Ag containing plasma which has a typical plasma protein distribution pattern. Line 2 represents the supernate after adjustment of the pH to 4.6 (step 2) and shows losses in fibrinogen and in the $\alpha_1$ protein region. Line 3 illustrates that a further lowering of contaminants (especially fibrinogen) is achieved by precipitation at 2% PEG (step 3). Line 4 illustrates that a large amount of proteins have been removed in the first 4.0 to 4.5% PEG supernate (step 4). From line 5 it can be seen that the resuspended HB Ag precipitate (step 5) still contains a relatively high quantity of protein contaminants and from line 6 it can be seen that the protein distribution pattern has not changed substantially after precipitating the bulk of PEG at a pH of approximately 5.0 (step 6). The second precipitation at 4.0 to 4.5% PEG concentration (step 7) removes substantial amounts of contaminants from the supernate as illustrated in line 7 and line 8 shows that the final precipitate of HB Ag (at two fold concentration) contains a major peak only in the $\alpha_2$ region and has two minor peaks in the albumin and fibrinogen regions (step 8).

The results of the foregoing purification steps are summarized in Table 1 wherein it is evident that: (1) In the pre-purification steps (steps 2, 3 and 4), 16% of the contaminating proteins are removed without loss of HB Ag; (2) The first 4.0 to 4.5% PEG precipitation (step 5) provides four fold purification; and (3) The second 4.0 to 4.5% PEG precipitation (step 8) provides a total of more than 24 fold purification of the HB Ag.

The factors which contribute to the improved results are: (1) the use of two successive precipitation steps at a PEG concentration of approximately 4.0 to 4.5 weight percent and an intermediate step wherein the pH is increased slightly to about 5.0 to obtain a precipitation of certain contaminants leads to a highly quantitative recovery of the antigen; (2) utilization of two pre-purification steps also contribute to the removal of interfering plasma protein contaminants; (3) titration with concentrated solutions instead of solid PEG leads to better control of purification conditions; and (4) lowering the temperature after each PEG addition results in lower PEG concentrations being required for selective and quantitative precipitation of HB Ag.

B. Purification of Hepatitis B Antigen On Hydroxy Apatite

Hepatitis B antigen prepared by precipitation with PEG as outlined above was further purified on hydroxy apatite. Because column chromatography on hydroxy apatite involves very slow flow rates, a batchwise procedure is preferably used. An additional 100 ml of distilled water are added to the product obtained in step 8 above to present a sample comprising approximately 200 ml of a fluid blood material containing approximately 500 mg of protein and having a HB Ag titer of 256–512 (CEP). The pH of the sample is adjusted to 6.8 by adding 10 ml of 0.5 M phosphate buffer. The solution is admixed with 150 ml of packed hydroxy apatite sediment and the admixture is stirred overnight at room temperature. The admixture is then centrifuged for two minutes at 2,000 rpm (in Sorvall) and the supernatant recovered. The sediment is washed twice with 100 ml of 0.02 M phosphate buffer at a pH of 6.8. The supernatant and the washings are pooled, concentrated by ultrafiltration and the volume adjusted to 12 ml using a 0.02 M phosphate buffer containing 0.02% sodium azide.

The washed sediment of hydroxy apatite is eluted twice with 100 ml of 0.1 M phosphate buffer at a pH of 6.8 and twice with 100 ml of a 0.2 M buffer. The eluates are pooled and concentrated by ultrafiltration and the buffer exchanged for 0.02 M phosphate at a pH of 6.8. Finally the sample is adjusted to 12 ml with a 0.02 M buffer containing 0.02% sodium azide.

The protein concentration is determined by measuring the O.D. at 280 nm (E=1.42) as illustrated in Table 2.

TABLE 2

| Sample | Volume | O.D. 280 nm | Protein mg/ml | Total Protein |
|---|---|---|---|---|
| Supernatant & washings 0.1 – 0.2 M phos- | 12 ml | 1662 (10 × dil) | 4.7 | 56 mgs |

TABLE 1

| PURIFICATION OF HB Ag WITH PEG 6000 | | | | | |
|---|---|---|---|---|---|
| STEP | MATERIAL | VOLUME (ml) | PROTEIN (g) | % ORIGINAL PROTEIN | HB Ag TITER (CEP) |
| 1 | Plasma | 240 | 14.2 | 100 | 256–512 |
| 2 | Plasma pH 4.6 | 240 | 13.2 | 93 | 256–512 |
| 3 | 2% PEG supernate | 250 | 12.0 | 84 | 256–512 |
| 4 | 4.5% PEG supernate | 270 | 8.2 | 58 | 0 |
| 5 | 4.5% PEG ppt | 200 | 3.6 | 25 | 256–512 |
| 6 | 4.5% PEG ppt pH 5.0 | 200 | 3.4 | 24 | 256–512 |
| 7 | 4.5% PEG supernate | 230 | 2.4 | 18 | 2–4 |
| 8 | 4.5% PEG ppt | 100 | 0.5 | 3.6 | 512–1024 |

TABLE 2-continued

| Sample | Volume | O.D. 280 nm | Protein mg/ml | Total Protein |
|---|---|---|---|---|
| phate eluates | 12 ml | 2.455 (10 × dil) | 17.3 | 208 mgs |

The antigenic activity was measured by CEP and the results are set forth in Table 3.

TABLE 3

| Sample | Volume | Total Protein | HB Ag titer |
|---|---|---|---|
| Initial HB Ag containing material subjected to hydroxy apatite adsorption | 200 ml | 500 mgs | 256 – 512 |
| Supernatant & washings 0.1 – 0.2 M phosphate | 12 ml | 56 mgs | 1024 – 2048 |
| eluates | 12 ml | 208 mgs | 1024 – 2048 |

The results given above show that approximately 50% of the HB Ag and only about 10% of the total protein was excluded from hydroxy apatite.

C. Isopycnic Banding of HB Ag by CsCl Density Gradient Centrifugation

The sample after PEG precipitation and hydroxy apatite treatment was further purified by isopycnic banding in CsCl density gradient. 208 mgs of protein with antigenic activity of 1024–2048 was mixed with CsCl powder to give a solution with density of 1.32 g/cc. A linear CsCl gradient (1.1–1.5 g/cc) was formed in Spinco at 35,000 rpm for 24 hours. Fractions of 10 drops were collected by dripping from the bottom. The fractions, after dilution to 0.5 ml with 0.05 Tris buffer having a pH of 7.5, were analyzed for protein by measuring the O.D. at 280 nm and the antigenic activity by CEP techniques.

Figure 2:
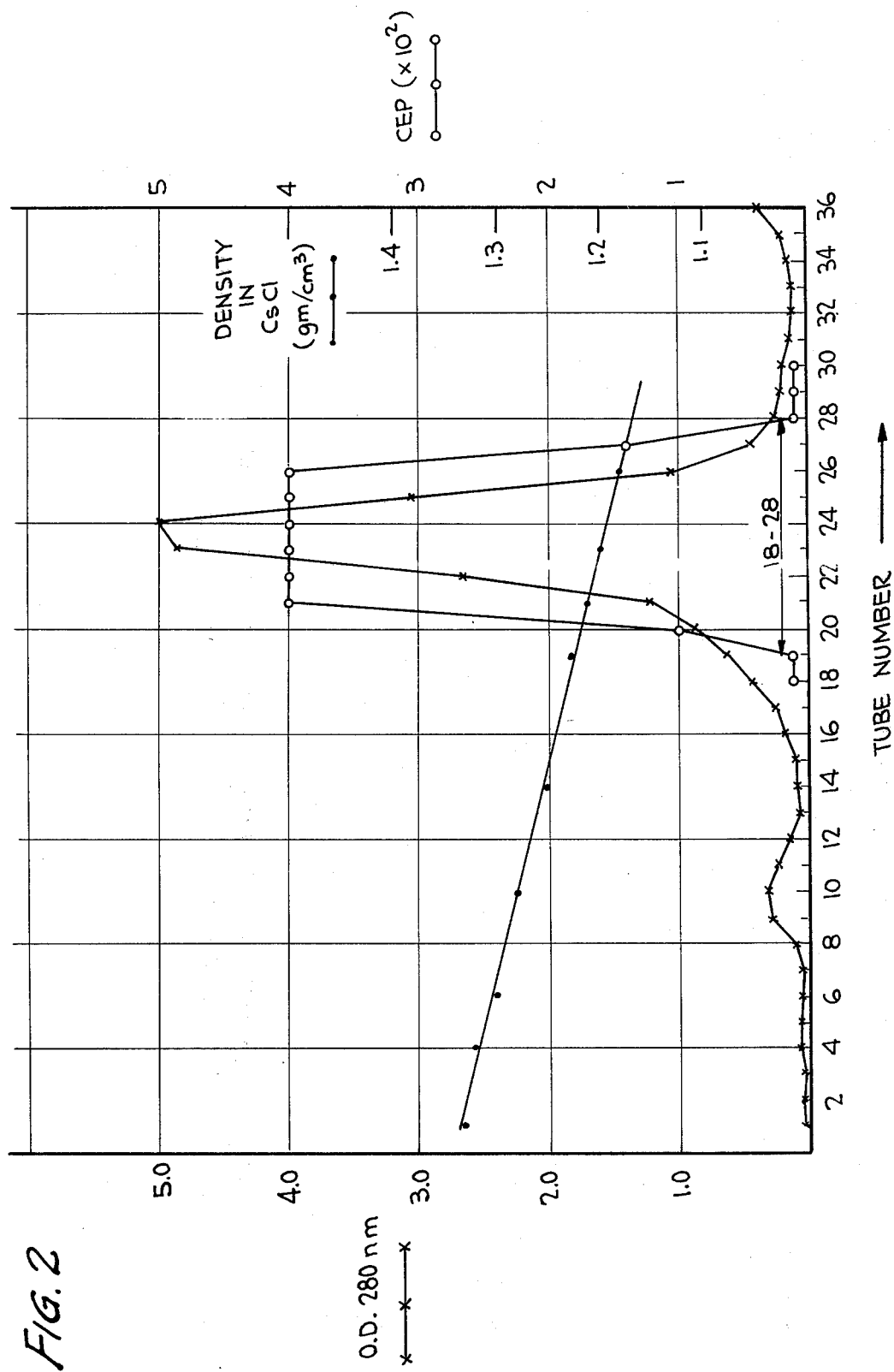
FIG. 2 is a graphical illustration of the results of the isopycnic banding steps of the invention.

The results of protein analysis (O.D. 280 nm), HB Ag activity (CEP) and CsCl density are illustrated in FIG. 2. The samples from the peak region of antigenic activity (fractions 18–28) were pooled, dialyzed and concentrated to 3 ml volume.

It is evident from the results shown in FIG. 2 that most of the high density protein contaminants (first O.D. peak) were removed by adsorption to hydroxy apatite.

D. Rate Zonal Centrifugation In Sucrose Gradient

Figure 3:
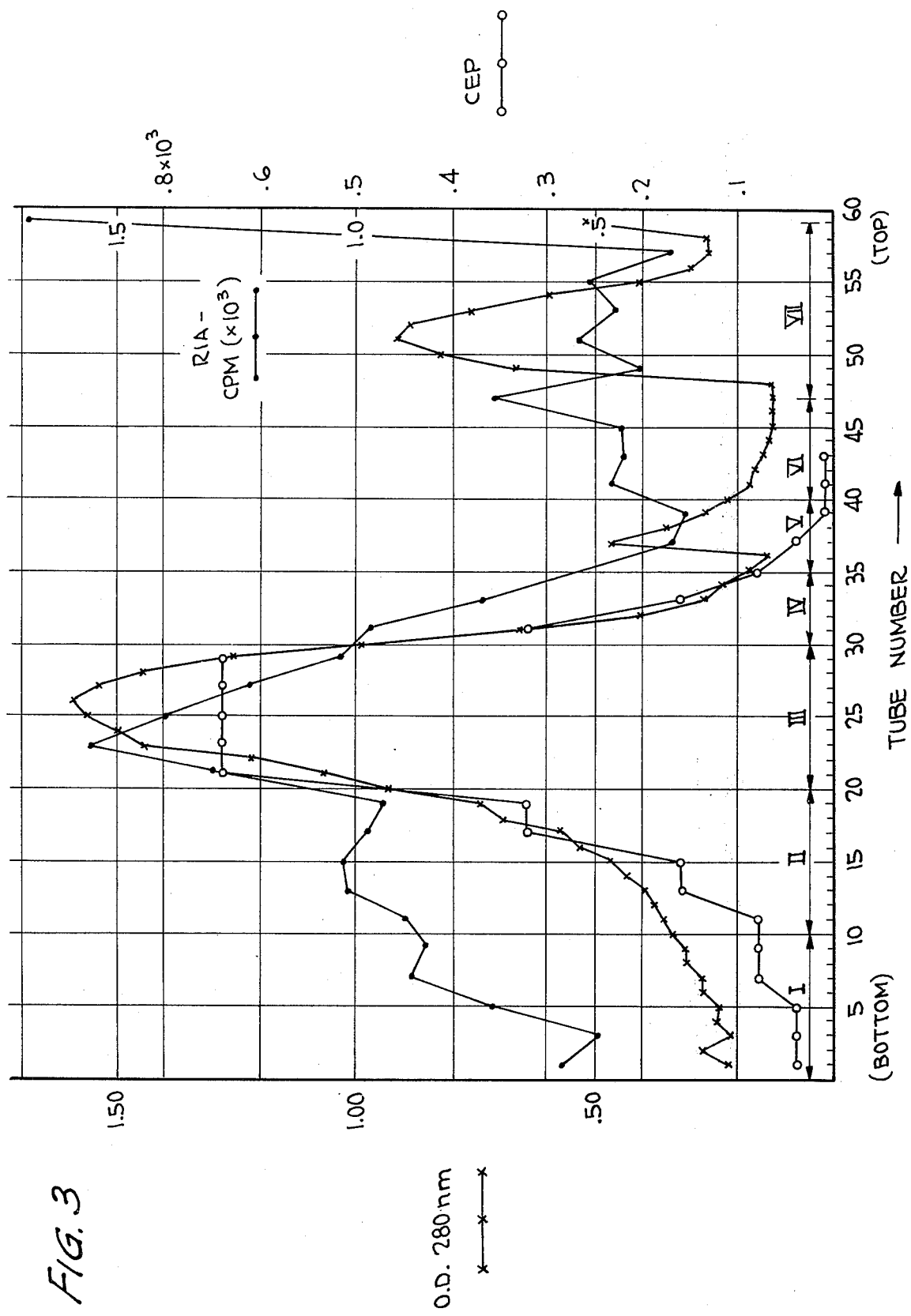
FIG. 3 is a graphical illustration of the results of the zonal ultracentrifugation step of the invention.

The sample, after PEG precipitation, hydroxy apatite treatment and isopycnic banding, was further purified by zonal ultracentrifugation. A linear sucrose gradient was prepared by mixing 14.5 ml each of solutions containing 25 weight percent and 10 weight percent sucrose in 0.02 M phosphate having a pH of 7.6 and containing 0.02 weight percent sodium azide. The sample was applied in three 1 ml aliquots and was centrifuged at 23,000 rpm for 18 hours. Fractions of approximately 0.5 ml each were collected by dripping from the bottom. The samples were analyzed for proteins by measuring the O.D. at 280 nm and the antigenic activity was determined by both CEP and RIA techniques. The results of the analyses are illustrated in FIG. 3. The eluate, according to FIG. 3, was pooled into seven fractions, dialyzed, and concentrated. There was only a small quantity of low molecular weight contaminants (two small O.D. peaks) which were distinctly separated from the large HB Ag containing peak (FIG. 3).

The concentrated fractions were further analyzed by immunoelectrophoresis. The pooled fractions I to IV did not show any serum-protein contaminants with antiserum against human serum proteins.

Analysis by electron microscopy of fractions I to IV revealed mostly short filaments in fraction I (FIG. 4), an average size of 27 nm round particles in fraction II (FIG. 5), mostly 20 nm particles in fraction III (FIG. 6) and 20 nm and smaller particles in fraction IV (not shown).

Figure 4:
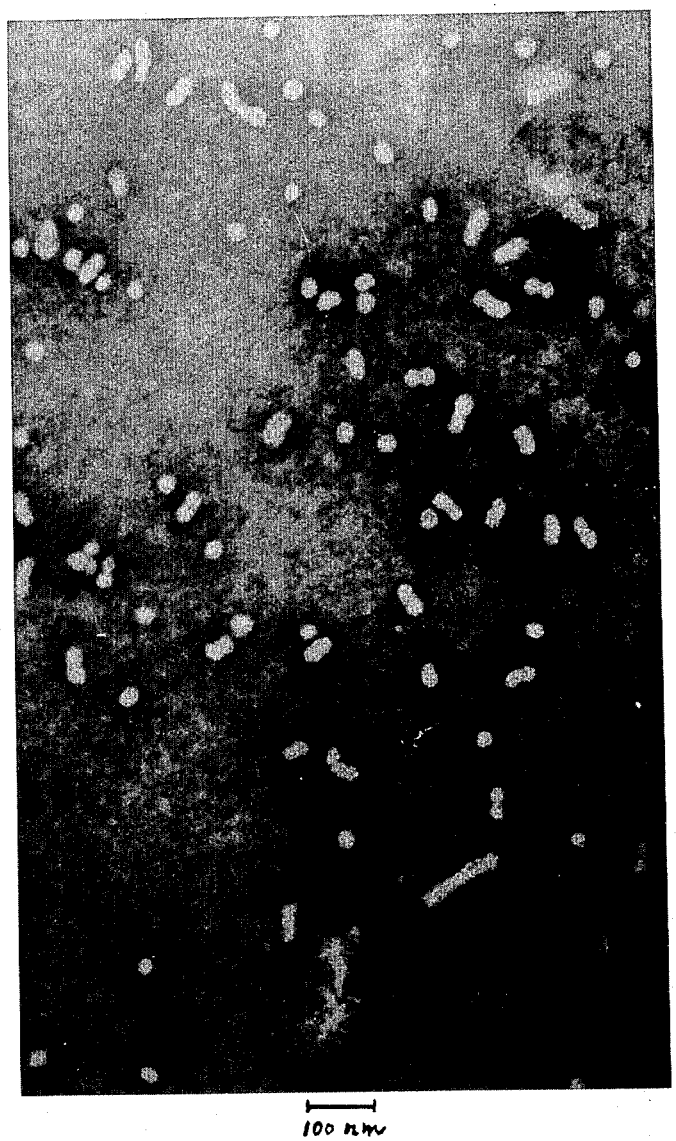
FIGS. 4, 5 and 6 are microphotographs illustrating products obtained after zonal ultracentrifugation.
Figure 5:
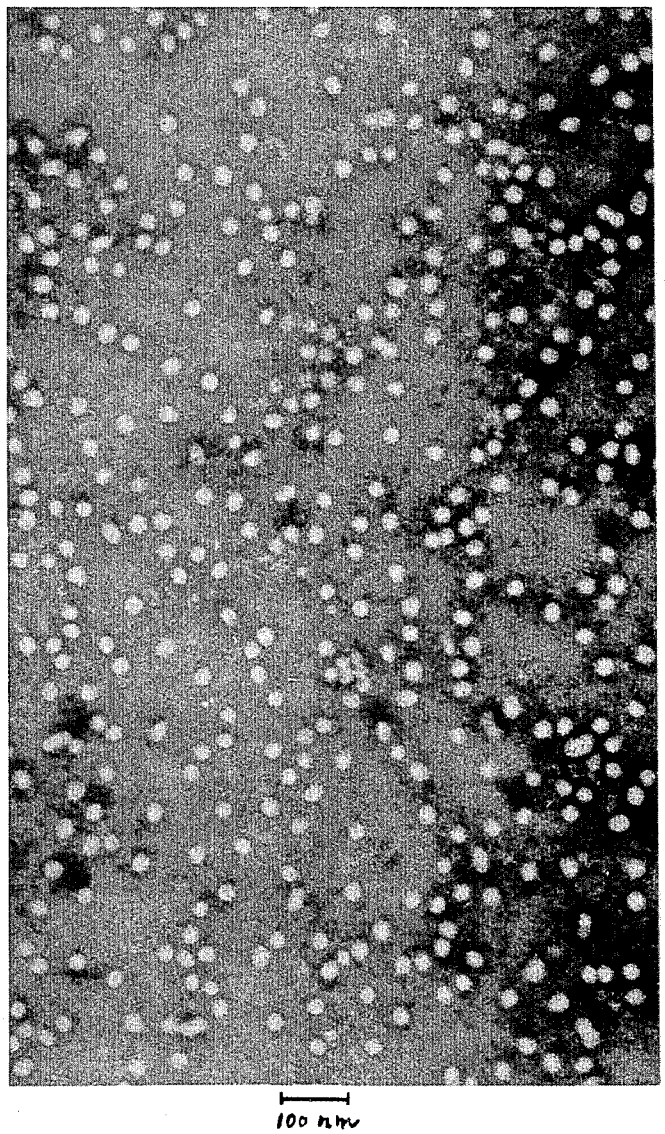
Figure 6:
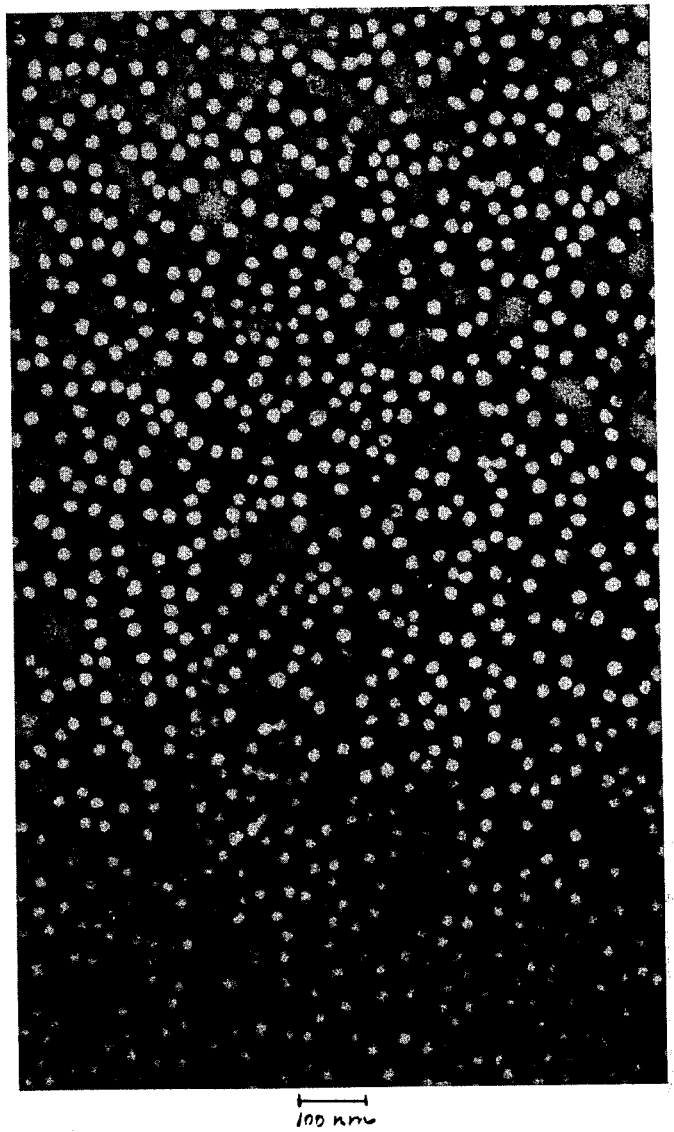

The results of the overall purification procedure can be followed in Table 4. It is evident from Table 4 that PEG precipitation resulted in more than a 24 fold purification of the HB Ag and a recovery of 83% of the original activity. The HB Ag is separated into two fractions by hydroxy apatite treatment. The supernate from the hydroxy apatite adsorption step, representing 40% of the original HB Ag activity, is further purified by isopycnic banding and rate zonal centrifugation. Fractions from the latter step are pooled as indicated in FIG. 3 and detailed analytical studies are carried out. These fractions contain no normal serum protein contaminants detectable by a sensitive immunoelectrophoresis technique. Further, they represent an HB Ag purification of 400–1200 fold and contain 43% of the starting activity. As can be seen in FIGS. 4–6, fraction I contains primarily short filaments, fraction II is composed mainly of spherical particles measuring 27 nm in diameter and fraction III contains typical 20 nm spheres.

TABLE 4

RESULTS OF PURIFICATION PROCEDURE

| STEP | SAMPLE | | VOLUME | TOTAL PROTEIN | TITER (CEP) | SPECIFIC ACTIVITY UNITS/MG | % RECOVERY |
|---|---|---|---|---|---|---|---|
| | Original Plasma | | 240 ml | 14.2 g[1] | 256–512 | 4.3–8.6 | 100 |
| I | 1st PEG Precipitate | | 200 ml | 3.6 g[1] | 256–512 | 14–28 | 83 |
| II | 2nd PEG Precipitate | | 100 ml | .5 g[1] | 512–1024 | 102–104 | 83 |
| III | Hydroxy Apatite Supernate | | 12 ml | 56 mg[2] | 1024–2048 | 205–410 | 40 |
| | Hydroxy Apatite Eluate | | 12 ml | 208 mg[2] | 1024–2048 | 51–102 | 40 |
| IV | Isopycnic Banding Of | | | 16.3 mg[3] | | 225–450 | |
| | Hydroxy Apatite Supernate | | 3 ml | 43.0 mg[2] | 3200–6400 | 600–1200 | 31 |
| V | Rate Zonal | Fraction I | 3 ml | 1.06[3] | 640–1280 | 1800–3600 | 3 |
| | | Fraction II | 2.5 ml | 1.93[3] | 1280 | 1600 | 5 |
| | | Fraction III | 3 ml | 6.84[3] | 6400–12800 | 2800–5600 | 31 |

TABLE 4-continued
RESULTS OF PURIFICATION PROCEDURE

| STEP | SAMPLE | VOLUME | TOTAL PROTEIN | TITER (CEP) | SPECIFIC ACTIVITY UNITS/MG | % RECOVERY |
|---|---|---|---|---|---|---|
| | Fraction IV | 3 ml | .45[3] | 800 | 5300 | 4 |

[1]Kjehldahl .1%
[2]$E_{1\ cm} = 1.42$ .1%
[3]$E_{1\ cm} = 3.73$

E. Large Scale Purification Of Hepatitis B Antigen Involving Hydroxy Apatite Chromatography Hepatitis B antigen was purified from 8 liters of chimpanzee plasma (type ad), 5 liters of human plasma (type adx) and 2 liters of human plasma (type ayx). The purification procedure comprises precipitation twice with polyethylene glycol in accordance with the procedures outlined above followed by column chromatography on hydroxy apatite. The results of purification of the chimpanzee antigen are presented for illustration.

a. Polyethylene Glycol Precipitation 800 ml of blood plasma is subjected to PEG precipitation in accordance with the method described above. All conditions are identical except for quantities of materials and sources of original plasma. The results of these procedures are set forth in Table 5 below.

TABLE 5

| Sample | Volume | HG Ag titer (CEP) | Protein (mg/ml) |
|---|---|---|---|
| Original plasma | 8000 ml | 1:500 | 55 |
| 2nd PEG precipitate | 250 ml | 1:10,000 | 52 |

Thus, a twenty fold purification has been achieved with respect to the HB Ag.

b. Column Chromatography

An aliquot (50 ml) sample of the second PEG ppt in H₂O is applied to a 500 ml column of hydroxy apatite and the column is eluted with a three step graduated eluant comprising an interrupted gradient of 0.02 M, 0.05 M and 0.10 M (1 liter each) phosphate buffers having a pH of 6.8. 10 ml fractions are collected. The HB Ag in the eluate is determined by CEP and the protein by measuring the O.D. at 280 nm. The results are presented in FIG. 7.

Figure 7:
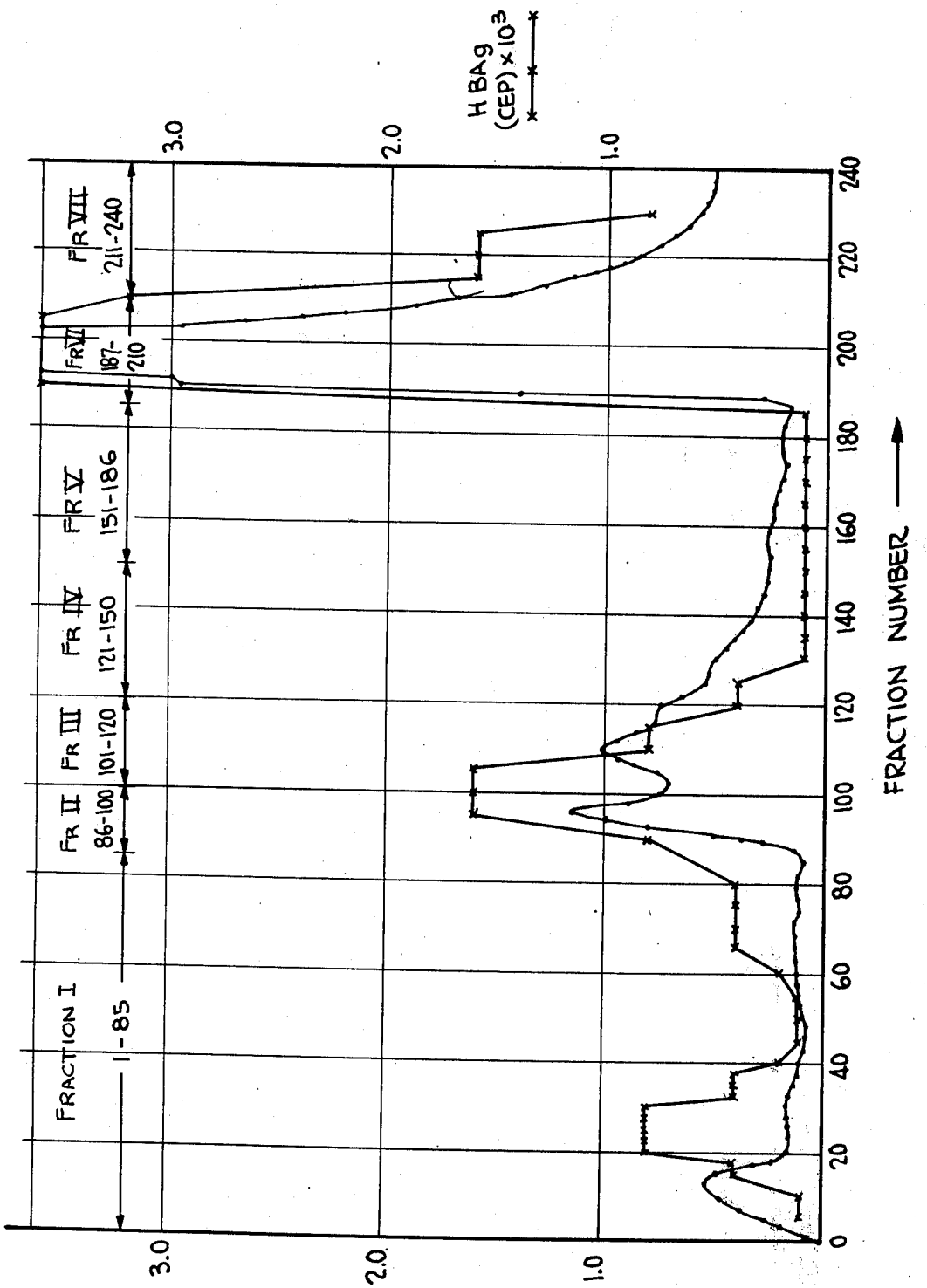
FIG. 7 is a graphical presentation of the results obtained by column chromatography.

The peak fractions of the eluate according to FIG. 7 are pooled, concentrated by ultra-filtration, and further analyzed. The results are summarized in Table 6. Electron microscopy of the first peak of HB Ag reveals mostly 25–30 nm particles, peak fraction II contains variable size particles including large filaments and 40 nm particles and peak fraction III contains mostly 20 nm particles.

TABLE 6

| SAMPLE | | VOLUME | HB Ag (CEP) | DILUTION | O.D. 280 nm | PROTEIN* mg/ml | TOTAL PROTEIN mg |
|---|---|---|---|---|---|---|---|
| Fraction I | (tubes 1–85) | 4 ml | 10,000 | 1:10 | 2.26 | 15.7 | 62.7 |
| Fraction II | (tubes 85–100) | 6 ml | 10,000 | 1:10 | 2.079 | 14.6 | 87.8 |
| Fraction III | (tubes 101–120) | 5 ml | 10,000 | 1:100 | 0.526 | 37.0 | 185.2 |
| Fraction IV | (tubes 121–150) | 6 ml | 800 | 1:10 | 2.620 | 18.5 | 110.7 |
| Fraction V | (tubes 151–186) | 6 ml | 800 | 1:10 | 1.730 | 12.2 | 73.1 |
| Fraction VI | (tubes 187–210) | 10 ml | 50,000 | 1:100 | 1.407 | 99.1 | 991.0 |
| Fraction VII | (tubes 211–240) | 7 ml | 12,000 | 1:100 | 0.691 | 48.7 | 340.6 |

0.1%
*E = 1.42

From the foregoing it is evident that column chromatography on hydroxy apatite serves a double purpose:
1. removing a large amount of protein contaminants; and
2. separation of three different populations of HB Ag particles.

We claim:

1. A process for producing highly purified type B hepatitis antigen from fluid blood material containing such antigen by substantially removing impurities from said material, said process comprising the steps of:
   maintaining the pH of said blood material within the range of approximately 4.4 to 4.7;
   admixing with said material, while its pH is being maintained within said range, approximately 4.0 to 4.5 weight percent polyethylene glycol based on the total weight of the admixture, to produce a precipitate containing type B hepatitis antigen;
   separately recovering said precipitate and adding a sufficient amount of water thereto to present an intermediate fluid material having a type B hepatitis antigen concentration substantially the same as in the original blood material;
   causing the pH of said intermediate fluid material to be within the range of approximately 4.9 to 5.1 to thereby produce a precipitate containing proteinaceous material and polyethylene glycol and a fluid phase containing type B hepatitis antigen;
   separately recovering said fluid phase and adjusting the pH thereof to within the range of approximately 4.4 to 4.7;
   admixing with said fluid phase, while maintaining its pH within said range, approximately 4.0 to 4.5 weight percent polyethylene glycol based on the total weight of the admixture, to produce a precipitate containing purified type B hepatitis antigen; and
   separately recovering said purified antigen containing precipitate.

2. A process as set forth in claim 1 wherein the temperature of each of the admixtures after each of said admixing steps is maintained within the range of approximately 0° to 8°C during the production of said precipitates.

3. A process as set forth in claim 1 wherein said original blood material contains fibrinogen, said process further comprising the steps of:
  admixing with said original blood material, while its pH is being maintained within said range of approximately 4.4 to 4.7, a fibrinogen precipitating quantity of polyethylene glycol amounting to 2.5 percent by weight of the total admixture or less, to produce a precipitate containing fibrinogen; and
  separating said precipitate from the remainder of the original blood material and discarding the precipitate.

4. A process as set forth in claim 3 wherein the temperature of each of the admixtures after each of said admixing steps is maintained within the range of approximately 0° to 8°C during the production of said precipitates.

5. A process as set forth in claim 1 wherein each of said separately recovering steps comprises centrifuging.

6. A process as set forth in claim 3 wherein is included, prior to said fibrinogen precipitating step, the steps of adjusting the pH of the original blood material to within said range of 4.4 to 4.7 and removing therefrom any precipitate which forms.

7. A process as set forth in claim 6 wherein each of said separately recovering steps, said separating step and said removing step comprise centrifuging.

8. A process as set forth in claim 1 wherein the polyethylene glycol used in each of said admixing steps is in the form of an aqueous solution.

9. A process as set forth in claim 8 wherein said polyethylene glycol solution contains approximately 30 percent polyethylene glycol by weight.

10. A process as set forth in claim 3 wherein the polyethylene glycol used in each of said admixing steps is in the form of an aqueous solution.

11. A process as set forth in claim 10 wherein said polyethylene glycol solution contains approximately 30 percent polyethylene glycol by weight.

12. A process as set forth in claim 1 wherein the antigen in said separately recovered purified antigen containing precipitate is further purified by adsorbing protein contaminants to hydroxy apatite followed, in series, by isopycnic banding and zonal ultracentrifugation.

13. A process as set forth in claim 1 wherein the antigen in said separately recovered purified antigen containing precipitate is further purified by hydroxy apatite adsorption.

14. A process as set forth in claim 13 wherein said adsorption is carried out utilizing column chromatographic procedures.

15. A process for producing highly purified type B hepatitis antigen from fluid blood material containing such antigen and for separating the latter into three different populations of particles, said process comprising:
  maintaining the pH of said blood material within the range of approximately 4.4 to 4.7;
  admixing with said material, while its pH is being maintained within said range, approximately 4.0 to 4.5 weight percent polyethylene glycol based on the total weight of the admixture, to produce a precipitate containing type B hepatitis antigen;
  separately recovering said precipitate and adding a sufficient amount of water thereto to present an intermediate fluid material having a type B hepatitis antigen concentration substantially the same as in the original blood material;
  causing the pH of said intermediate fluid material to be within the range of approximately 4.9 to 5.1 to thereby produce a precipitate containing proteinaceous material and polyethylene glycol and a fluid phase containing type B hepatitis antigen;
  separately recovering said fluid phase and adjusting the pH thereof to within the range of approximately 4.4 to 4.7;
  admixing with said fluid phase, while maintaining its pH within said range, approximately 4.0 to 4.5 weight percent polyethylene glycol based on the total weight of the admixture, to produce a precipitate containing purified type B hepatitis antigen;
  separately recovering said purified antigen containing precipitate; and
  subjecting said purified antigen containing precipitate to hydroxy apatite adsorption in a chromatographic column using a three step graduated eluant.

* * * * *